United States Patent

Stephen

[11] 4,000,112
[45] Dec. 28, 1976

[54] HINDERED PHENOL DERIVATIVES OF 9-THIABICYCLONONANES AND STABILIZED COMPOSITIONS

[75] Inventor: John F. Stephen, New City, N.Y.

[73] Assignee: Ciba-Geigy Corporation, Ardsley, N.Y.

[22] Filed: May 27, 1975

[21] Appl. No.: 581,189

Related U.S. Application Data

[63] Continuation-in-part of Ser. No. 558,985, March 17, 1975, abandoned.

[52] U.S. Cl. .................. 260/45.8 RW; 252/482; 252/57; 260/45.85 S; 260/327 TH; 260/332.1; 260/332.3 R; 260/800
[51] Int. Cl.² .................. C08K 5/45; C07D 335/00
[58] Field of Search ..... 260/800, 327 TH, 332.1 R, 260/332.3 R, 45.8 RW, 45.85 S; 252/48.2, 57

[56] References Cited

UNITED STATES PATENTS

| | | | |
|---|---|---|---|
| 2,514,210 | 7/1950 | Albert | 260/45.95 C |
| 2,662,061 | 12/1953 | Gilcrease et al. | 260/45.95 C |
| 3,149,093 | 9/1964 | Hecker | 260/45.95 C |
| 3,168,480 | 2/1965 | Worrel | 260/45.95 C |
| 3,256,361 | 6/1966 | Harding et al. | 260/45.95 C |
| 3,546,164 | 12/1970 | Stewart et al. | 260/45.95 C |
| 3,644,415 | 2/1972 | Weil et al. | 260/327 TH |

*Primary Examiner*—V.P. Hoke
*Attorney, Agent, or Firm*—Luther A. R. Hall

[57] ABSTRACT

The 9-thiabicyclononane derivatives have the formula

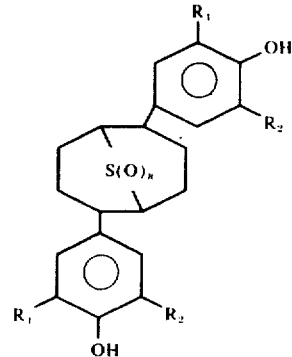

or

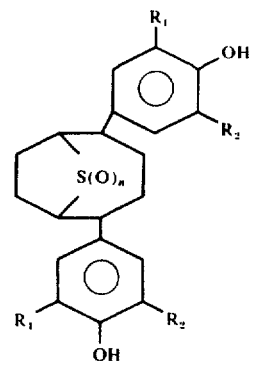

wherein $R_1$ and $R_2$ are each independently tertiary alkyl of 4 to 8 carbon atoms or $\alpha,\alpha$-dimethylbenzyl, and $n$ is 0 to 2.

The 9-thiabicyclononanes are prepared by reacting an alkali salt of 2,6-di-tert-alkylphenols with 2,6-dichloro-9-thiabicylo[3.3.1]nonane in a dipolar aprotic solvent. The sulfoxide and sulfones are prepared from the sulfides by oxidation with peracids.

The compounds are useful as stabilizers for organic materials, particularly turbine oils and polyolefins, subject to oxidative degradation.

14 Claims, No Drawings

HINDERED PHENOL DERIVATIVES OF 9-THIABICYCLONONANES AND STABILIZED COMPOSITIONS

This application is a Continuation-in-Part of copending application, Ser. No. 558,985, filed Mar. 17, 1975, now abandoned.

DETAILED DISCLOSURE

This invention pertains to 9-thiabicyclononanes substituted with hindered phenolic moieties and to organic materials normally subject to oxidative, thermal and UV light degradation stabilized with said 9-thiabicyclononane compounds.

More specifically the compounds of this invention are those having the formula

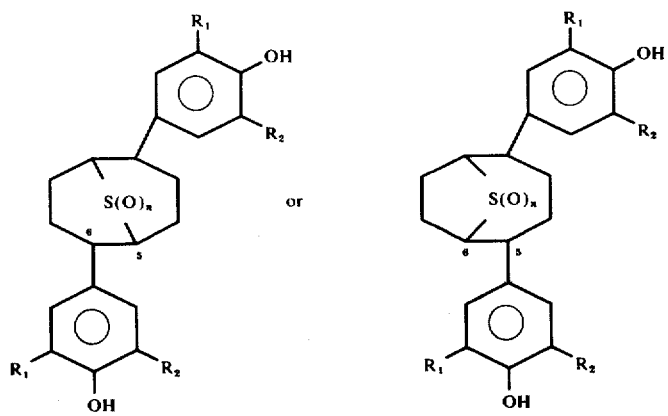

wherein $R_1$ and $R_2$ are each independently tertiary alkyl of 4 to 8 carbon atoms, or $\alpha,\alpha$-dimethylbenzyl, and $n$ is 0 to 2.

Where the molecule contains a hindered phenol moiety attached to carbon atom 6, the sulfur atom is attached to carbon atom 5. Such molecules are substituted 9-thiabicyclo[3.3.1]nonanes. In the reverse case where the molecule contains a hindered phenol moiety attached to carbon atom 5, the sulfur atom is bonded to carbon atom 6. Such molecules are substituted 9-thiabicyclo[4.2.1]nonanes.

Mixtures of these different nonanes are also part of this invention for both isomeric structures have desired stabilization effectiveness. During the preparation of these 9-thiabicyclononanes, mixtures of the above cited isomers are normally obtained. There is no reason to separate the isomers to carry out one objective of this invention namely to provide stabilization to organic materials in need thereof.

The [3.3.1]nonane and the [4.2.1]nonane isomers can be readily separated from one another by conventional recrystallization or chromatographic procedures from any of their sulfide, sulfoxide or sulfone mixtures. Alternately, the separation of the isomers can be carried out on the sulfide mixture, or optionally on the sulfoxide mixture, with subsequent oxidation steps to the sulfoxide or sulfone being carried out on the separated [3.3.1] or [4.2.1]nonane isomer.

$R_1$ and $R_2$ can be independently tert-alkyl of 4 to 8 carbon atoms or $\alpha,\alpha$-dimethylbenzyl. Preferably $R_1$ and $R_2$ are independently tertiary alkyl of 4 to 8 carbon atoms such as tert-butyl, tert-amyl or tert-octyl. Most preferably $R_1$ and $R_2$ are each tert-butyl.

$n$ has a value of 0 to 2 representing wherein $n$ is 0 the sulfide, where $n$ is 1 the sulfoxide and where $n$ is 2 the sulfone. Preferably $n$ is 0 to 1 when these compounds are used to stabilize hydrocarbon, mineral or turbine oils.

The hindered phenol intermediates needed to prepare the compounds of this invention are either commercially available such as 2,6-di-tert-butylphenol or can be readily prepared by the aluminum catalyzed alkylation of phenol with the appropriate olefin such as 2-methyl-1-butene or 2,4,4-trimethyl-1-pentene.

The other key intermediate is 2,6-dichloro-9-thiabicyclo[3.3.1]nonane which can be made from cis,cis-1,5-cyclooctadiene and sulfur dichloride. These starting materials are commercially available. The preparation of 2,6-dichloro-9-thiabicyclo[3.3.1]nonane is described by E. J. Corey et al, J. Org. Chem, 31,663(1966); E. D. Weil et al, J. Org. Chem, 31,1669(1966); F. Lautenschlaeger, Can. J. Chem, 44,2813(1966). The teachings of these publications are hereby incorporated by references in regards the preparation of 2,6-dichloro-9-thiabicyclo[3.3.1]nonane. This preparation is outlined below.

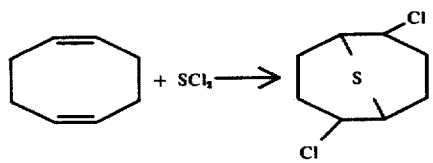

in making the compounds of this invention, the 2,6-dichloro-9-thiabicyclo[3.3.1]nonane is reacted with two moles of an alkali metal salt of the appropriate 2,6-di-tert-alkylphenol in a dipolar aprotic solvent to give a mixture of the corresponding 2,6-bis(3,5-di-tert-alkyl-4-hydroxyphenyl)-9-thiabicyclo[3.3.1]nonane and 2,5-bis(3,5-di-tert-alkyl-4-hydroxyphenyl)-9-thiabicyclo[4.2.1]nonane.

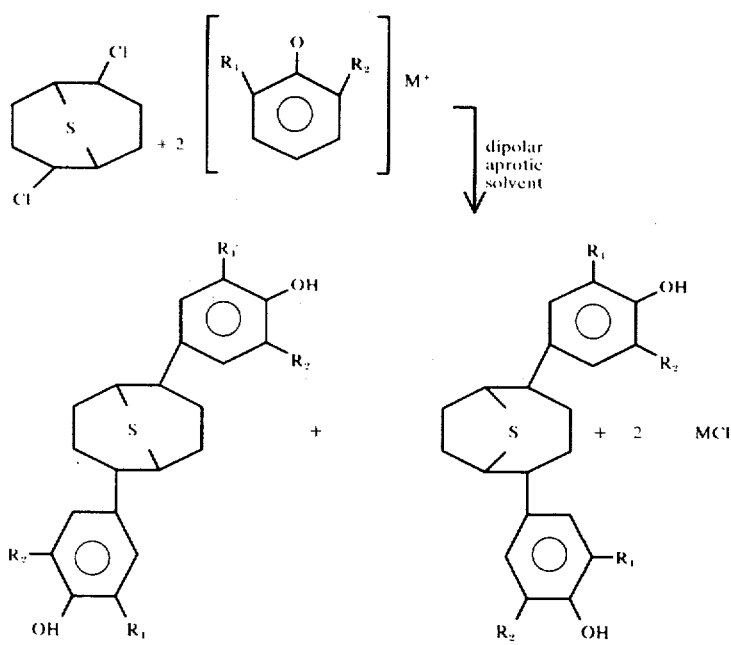

Suitable alkali metal salts for M include potassium, sodium and lithium salts. Where M is sodium is preferred.

The class of dipolar aprotic solvents suitable for use in making the compounds of this invention include N,N-dimethylformamide, N,N-dimethylacetamide, N-methylpyrrolidone, dimethyl sulfoxide, hexamethylphosphoramide, tetramethylurea and sulfolane.

It is noted that the synthetic procedure used to prepare the sulfide compounds of this invention leads to a mixture of both the [3.3.1]nonanes and the [4.2.1]-nonanes. Since neither the structure of the isomer nor the distribution of the isomers has any adverse effect on the stabilizing activity, it is unnecessary to separate these position isomers. This invention comprises both the [3.3.1]nonanes and the [4.2.1]nonanes separately as well as mixtures thereof. Likewise another object of this invention comprises organic materials stabilized with the [3.3.1]nonanes and [4.2.1]nonanes separately or with mixtures of said nonanes.

The 9-oxides (or sulfoxides) and the 9,9-dioxides (or sulfones) of this invention are prepared by oxidizing the appropriate sulfide with a suitable sulfur oxidizing agent. Peracids such as peracetic acid or m-chloroperbenzoic acid are admirably suited for this purpose.

The hindered phenol derivatives of 9-thiabicyclononanes of this invention are stabilizers of organic material normally subject to thermal and oxidative deterioration. Materials which are thus stabilized include synthetic organic polymeric substances such as poly-α-olefins, polyethylene, polypropylene, cross-linked polyethylene, polybutylene including copolymers of α-olefins such as ethylene/propylene copolymer; dienes such as polubutadiene, polyisoprene, and the like, including copolymers with other monomers; polyurethanes and polyamides such as polyhexamethylene adipamide and polycaprolactam; polyesters such as polyethylene terephthalates; polycarbonates; polyacetals; unsaturated polyesters; polystyrene, polyethylene oxide; and copolymers such as those of high impact polystyrene containing copolymers of butadiene and styrene and those formed by the copolymerization of acrylonitrile, butadiene and/or styrene, ABS; SAN; natural and synthetic rubbers such as ethylene/propylene/diene copolymer (EPDM) and chlorinated rubber; polyphenylene oxide and copolymers; vinyl resins formed from the polymerization of vinyl halides or from the co-polymerization of vinyl halides with unsaturated polymerizable compounds, e.g., vinyl esters, α,β-unsaturated aldehydes, α,β-unsaturated ketones and unsaturated hydrocarbons such as butadienes and styrene; and plasticized polyvinyl chloride.

Other materials which can be stabilized by the compounds of the present invention include lubricating oil of the aliphatic ester type, i.e., di(2-ethylhexyl) azelate and other synthetic ester lubricants, pentaerythritol tetracaproate, and the like, spinning lubricants of the polyester type; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, mineral lube oils, cutting fluids, waxes, resins and the like, salts of fatty acids such as soaps and the like; and alkylene glycols, e.g., β-methoxyethylene glycol, methoxytriethylene glycol, triethylene glycol, octaethylene glycol, dibutylene glycol, dipropylene glycol and the like.

The 9-thiabicyclononane derivatives of this invention exhibit good stabilization activity in polypropylene particularly in the presence of a thio ester co-stabilizer such as distearyl β-thiodipropionate (DSTDP).

Thus, substrates of particular importance are olefin polymers such as polyethylene, polypropylene, olefin copolymers and blends thereof, especially polypropylene.

The 9-thiabicyclononane derivatives of this invention, particularly the sulfide and sulfoxide members, further provide particularly outstanding stabilization protection to hydrocarbon oils, mineral oils, turbine oils and the like which undergo thermal and oxidative degradation. The compounds of this invention not only inhibit the premature formation of undesirable corrosive acidity in mineral turbine oils containing said compounds as stabilizers, but also provide exceptional non-sludging properties to these oils. These properties are highly desirable in the longterm usage of turbine oil systems, and any stabilizer providing such a combination of useful and valuable properties in hydrocarbon oils would find ready utility therein.

The 9-thiabicyclononanes of this invention provide superior oxidative stabilization to hydrocarbon oils when compared to widely used commercial antioxidants such as BHT, (2,6-di-tert-butyl-4-methylphenol).

The 9-thiabicyclononanes of this invention are also effective processing stabilizers for polyolefin polymers even at very low concentrations (0.02% by weight) and are fully comparable in this use to commercial antioxidants such as BHT.

In general, the stabilizers of this invention are employed from about 0.01 to about 5% by weight of the stabilized composition, although this will vary with the particular substrate and application. An advantageous range is from about 0.05 to about 2% and especially from about 0.1 to about 1%.

For addition to polymeric substrates, the stabilizers can be blended before polymerization or after polymerization, during the usual processing operations, for example, by dry blending, extruder compounding and hot-milling. The composition then can be extruded, pressed, injection molded or otherwise fabricated into films, fibers, filaments, molded items and the like. The heat stabilizing properties of these compounds advantageously stabilize the polymer against degradation during such processing at the high temperature generally encountered. However, the useful life of polymeric materials is also extended by these stabilizers far beyond their ability to survive processing.

The stabilizers can also be dissolved in suitable solvents and sprayed on the surface of films, fabrics, filaments or the like to provide effective stabilization.

These compounds can also be used in combination with other additives such as sulfur-containing esters, e.g., distearyl β-thiodipropionate (DSTDP) in an amount of from 0.01 to 2% by weight of the organic material, and the like, pourpoint depressants, corrosion and rust inhibitors, dispersing agents, emulsifiers, antifoaming agents, carbon black, accelerators and other chemicals used in rubber compounding, plasticizers, color stabilizers, antistatic agents, antislip agents, antiblock agents, surface active agents, fillers, organophosphites, organothiophosphites, heat stabilizers, ultraviolet light stabilizers, antiozonants, dyes, pigments, metal deactivators, metal chelating agents, dyesites and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

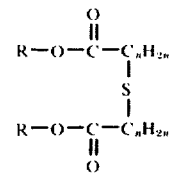

wherein R is an alkyl group having from 6 to 24 carbon atoms; and n is an integer from 1 to 6. Especially useful compounds of this type are dilauryl β-thiodipropionate and distearyl β-thiodipropionate. The above co-stabilizers are used in the amount of from 0.01 to 2% by weight of the organic material, and preferably from 0.1 to 1%.

In addition to the above noted additives that can be employed in combination with the compounds of this invention, it is often especially advantageous to employ also light stabilizers. The light stabilizers are used in the amount of from 0.01 to 5% by weight of the organic material, and preferably from 0.1 to 1%. Illustrative examples of light stabilizers are listed below.

UV-ABSORBERS AND LIGHT PROTECTION AGENTS 2-(2'-hydroxyphenyl)-2H-benztriazoles, such as, for example, the 5'-methyl-; 3',5'-di-tert-butyl-; 5'-tert'butyl-; 5'-(1,1,3,3-tetramethylbutyl)-; 5-chloro-3',5'-di-tert-butyl-; 5-chloro-3'-tert-butyl-5'-methyl; 3'-sec-butyl-5'tert-butyl-; 3'-[α-methylbenzyl]-5'-methyl-; 3'-[α-methylbenzyl]-5'-methyl-5-chloro-; 4'-hydroxy-; 4'-methoxy-; 4'-octoxy-; 3',5'-di-tert-amyl-; 3'-methyl-5'-carbomethoxyethyl-; 5-chloro-3',5'-di-tert-amyl- or 4'-tert-octyl- derivatives.

2,4-bis-(2'-hydroxyphenyl)-6-alkyl-s-triazines, such as, for example, the 6-ethyl-, 6-undecyl- or 6-heptadecyl- derivatives.

2-hydroxybenzophenones, such as, for example, the 4-hydroxy-, 4-methoxy-, 4-octoxy-, 4-decyloxy, 4-dodecyloxy-, 4-benzyloxy-, 4,2', 4'-trihydroxy- or 2'-hydroxy-4,4'-dimethoxy- derivatives.

1,3-bis-(2'-hydroxybenzoyl)benzenes, such as, for example, 1,3-bis-(2-hydroxy-4'-hexyloxybenzoyl)-benzene, 1,3-bis-(2'hydroxy-4'-octoxybenzoyl)benzene and 1,3-bis-(2'-hydroxy-4'-dodecyloxybenzoyl)benzene.

Esters of optionally substituted benzoic acids, such as, for example, phenyl salicylate, octylphenyl salicylate, dibenzoylresorcinol, bis-(4-tert-butyl-benzoyl)-resorcinol, benzoylresorcinol, 3,5-di-tert-butyl-4-hydroxybenzoic acid 2,4-di-tert-butylphenyl ester, octadecyl ester or 2-methyl-4,6-di-tert-butyl-phenyl ester, and the alkyl esters of 4-(3,5-di-tert-butyl-4-hydroxybenzoyloxy)-3,5-di-tert-butylbenzoic acid.

Acrylates, such as, for example, α-cyano-β,β-diphenyacrylic acid ethyl ester or isooctyl ester, α-carbomethoxycinnamic acid methyl ester, α-cyano-β-methyl-p-methoxycinnamic acid methyl ester or butyl ester and N-(β-carbomethoxy-vinyl)-2-methylindoline.

Nickel compounds, such as for example, nickel complexes of 2,2'-thio-bis-4-(1,1,3,3-tetramethylbutyl)-phenol, such as the 1:1 and 1:2 complex, optionally with other ligands such as n-butyl-, triethanol-, cyclohexyl- or N-cyclohexyldiethanolamine; nickel complexes of bis-[2-hydroxy-5-(1,1,3,3-tetramethylbutyl)-phenyl]sulfone, such as the 2:1 complex, optionally with other ligands such as 2-ethylcaproic acid; nickel dibutyldithiocarbamate, nickel salts of 4-hydroxy-3,5-di-tert-butylbenzyl-phosphonic acid monoalkyl esters, such as the methyl, ethyl or butyl ester, the nickel complex of (2-hydroxy-4-methyl-phenyl)-undecylketonoxime and nickel 3,5-di-tert-butyl-4-hydroxybenzoate.

Oxalic acid diamides, such as, for example, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-5-tert-butyl-2'-ethloxanilide, 2-ethoxy-2'-ethyloxanilide, N,N'-bis-(3-dimethylaminopropyl)oxalamide, mixtures of o- and p-methoxy and o- and p-ethoxy-di-substituted oxanilides and mixtures of 2-ethoxy-5-tert-butyl-2'-ethyloxanilide with 2-ethoxy-2'-ethyl-5,4'-di-tert-butyloxanilide.

Sterically hindered amines, such as, for example, 4-benzoyloxy-2,2,6,6-tetramethylpiperidine, 4-stearoyloxy 2,2,6,6-tetramethylpiperidine, bis-(2,2,6,6-tetramethylpiperidyl) sebacate and 3-n-octyl-7,7,9,9-tetramethyl-1,3,8-triazaspiro[4,5] decan-2,4-dione.

For exemplification purposes only are listed below compounds of this invention which are useful as stabilizers as discussed above:

2,6-bis(3,5-di-tert-amyl-4-hydroxyphenyl)-9-thiabicyclo-[3.3.1]nonane 2,5-bis(3,5-di-tert-amyl-4-hydroxyphenyl)-9-thiabicyclo-[4.2.1]nonane 2,6-bis(3,5-di-tert-octyl-4-hydroxyphenyl)-9-thiabicyclo-[3.3.1]nonane 2,5-bis(3,5-di-tert-octyl-4-hydroxyphenyl)-9-thiabicyclo-[4.2.1]nonane 2,6-bis(3,5-di-tert-amyl-4-hydroxyphenyl)-9-thiabicyclo-[3.3.1]nonane-9-oxide 2,5-bis(3,5-di-tert-amyl-4-hydroxyphenyl)-9-thiabicyclo-[4.2.1]nonane-9,9-dioxide 2,6-bis(3,5-di-tert-octyl-4-hydroxyphenyl)-9-thiabicyclo-[3.3.1]nonane-9-oxide 2,5-bis[3,5-bis(α,α-dimethylbenzyl)-4-hydroxyphenyl]-9-thiabicyclo[4.2.1]nonane-9,9-dioxide The following examples are illustrative of the invention, but are not meant to limit the scope of the same in any fashion.

EXAMPLE 1

2,6-Bis(3,5-di-tert-butyl-4-hydroxyphenyl)-9-thiabicyclo[3.3.1]nonane and
2,5-Bis(3,5-di-tert-butyl-4-hydroxyphenyl)-9-thiabicyclo[4.2.1]nonane Mixture and Pure Isomers Under a nitrogen atmosphere, a solution of 98.4% sodium hydroxide (24.4 grams, 0.60 mole) in 20 ml of water was added with stirring and cooling to a solution of 2,6-di-tert-butylphenol (130.0 grams, 0.63 mole) in 255 ml. of N,N-dimethylformamide. The reaction mixture was stirred for 50 minutes at 20°–25° C and then distilled. A mixture of N,N-dimethylformamide and water was distilled from the mixture at a boiling point of 30°–43° C at 12 mm of Hg. Some 125 ml of distillate was collected. After cooling to 20° C and reimposing a nitrogen atmosphere, a solution of 2,6-dichloro-9-thiabicyclo[3.3.1]nonane (63.3 grams, 0.30 mole) in 300 ml. of N,N-dimethylformamide was added over a 10-minute period. During the course of the next 50 minutes the temperature rose to 50° C. The reaction mixture was then heated at 45°–50° C for 18 hours. A few drops of concentrated hydrochloric acid were then added to the cooled solution to discharge the color. 250 ml. of water were then added to dissolve the solid sodium chloride present and to precipitate the desired crude product which was collected by filtration. The solid thus obtained was slurried with 350 ml of methanol. The mixture was then heated to boiling for 5 minutes. After cooling, a mixture of the desired titled compounds was isolated in a yield of 95.0 grams by filtration. Recrystallization of the mixture from acetone gave 54.2 grams of a purified mixture melting at 233°–242° C. NMR analysis indicated the product consisted of 75% of the [3.3.1]nonane isomer and 25% of the [4.2.1]nonane isomer. (Compound 1 = Mixture)

Calc'd for $C_{36}H_{54}O_2S$:C, 78.49; H, 9.88; S, 5.82. Found: C, 78.55; H, 9.64; S, 5.68.

When the Compound 1 mixture was recrystallized several times from benzene-hexane solution, the [3.3.1]isomer 2,6-bis(3,5-di-tert-butyl-4-hydroxyphenyl)-9-thiabicyclo[3.3.1]nonane, was isolated as a pure product, melting at 247°–250° C following a final recrystallization from acetone.

The [4.2.1]isomer, 2,5-bis(3,5-di-tert-butyl-4-hydroxyphenyl)-9-thiabicyclo[4.2.1]nonane is isolated from the above benzene-hexane mother liquors by further recrystallizations.

2,6-DICHLORO-9-THIABICYCLO[3.3.1]NONANE

A solution of 258 grams (2.5 moles) of sulfur dichloride in 300 ml of hexane was added dropwise over a 1.5-hour period to a stirred solution of 216.4 grams (2.0 moles) of 1,5-cyclooctadiene in 500 ml of hexane at 15° C. During the addition the temperature was maintained at 15°–18° C. After the addition of the sulfur dichloride solution was complete, the reaction mixture was stirred at 15°–18° C for 1 hour. The 2,6-dichloro-9-thiabicyclo[3.3.1]-nonane, which separated from solution, was collected by filtration in a yield of 338 grams and had a melting point of 97°–99° C.

When in Example 1, an equivalent amount of 2,6-di-tert-octylphenol is substituted for the 2,6-di-tert-butylphenol, a mixture of 2,6-bis(3,5-di-tert-octyl-4-hydroxyphenyl)-9-thiabicyclo[3.3.1]nonane and 2,5-bis(3,5-di-tert-octyl-4-hydroxyphenyl)-9-thiabicyclo[4.2.1]nonane is obtained.

When in Example 1, the 2,6-di-tert-butylphenol is replaced by an equivalent amount of 2,6-di-tert-amylphenol, a mixture of 2,6-bis(3,5-di-tert-amyl-4-hydroxyphenyl)-9-thiabicyclo[3.3.1]nonane and 2,5-bis(3,5-di-tert-amyl-4-hydroxyphenyl)-9-thiabicyclo[4.2.1]nonane is obtained.

EXAMPLE 2

2,6-Bis(3,5-di-tert-butyl-4-hydroxyphenyl)-9-thiabicyclo[3.3.1]nonane-9-oxide and
2,5-Bis(3,5-di-tert-butyl-4-hydroxyphenyl)-9-thiabicyclo[4.2.1]nonane-9-oxide Mixture and Pure Isomers A solution of 85% m-chloroperbenzoic acid (4.07 grams, 0.02 mole) in 75 ml. of methylene chloride was added dropwise over a 20-minute period to a stirred solution of the mixture of isomers prepared in Example 1 (10.9 grams, 0.02 mole) in 50 ml. of methylene chloride at 10° C. After the addition was complete, the reaction mixture was stirred for 10 minutes at 10° C. A 5% aqueous sodium carbonate solution was then added, and the two layers separated. The organic layer was washed with water, dried over anhydrous sodium sulfate, filtered and evaporated under reduced pressure to yield a glassy residue. This residue was recrystallized from ether to give 10.2 grams of the desired sulfoxide mixture. A recrystallization from aqueous acetone afforded 6.1 grams of a purified sulfoxide mixture melting at 255°–258° C (dec.). (Compound 2 = Mixture) Calc'd for $C_{36}H_{54}O_3S$: C, 76.27; H, 9.60; S, 5.66. Found: C, 76.12; H, 9.85; S, 5.64.

SEPARATION OF ISOMERS

A TLC analysis (silica gel, benzene/chloroform/ethyl acetate 40/40/20) of the Compound 2 mixture indicated two components with $R_f$ values of 0.42 and 0.27 respectively.

A 10-gram portion of the Compound 2 mixture was subjected to dry column chromatography (silica gel with chloroform/ethyl acetate 100/0.5 used as a developing solvent). Fractions with $R_f$ 0.42 values were combined and the material was extracted from the silica gel using a methylene chloride/ether mixture. Evaporation of the solvent gave 4.2 grams of 2,6-bis(3,5-di-tert-butyl-4-hydroxyphenyl)-9-thiabicyclo[3.3.1]nonane-9-oxide. A sample recrystallized from ether melted at 282°–286° C (dec.). The bicyclo[3.3.1]nonane structure for this pure product was affirmed by its NMR spectrum.

Fractions containing material with $R_f$ 0.27 values were combined and the material was also extracted from the silica gel with a methylene chloride/ether mixture. Evaporation of the solvent and recrystallization of the resulting solid residue from aqueous methanol yielded 0.5 gram of 2,5-bis-(3,5-di-tert-butyl-4-hydroxyphenyl)-9-thiabicyclo[4.2.1]-nonane-9-oxide, melting at 268°–271° C (dec.). The bicyclo[4.2.1]-nonane structure for this pure isomer was confirmed by its NMR spectrum.

EXAMPLE 3

2,6-Bis(3,5-di-tert-butyl-4-hydroxyphenyl)-9-thiabicyclo[3.3.1]nonane-9,9-dioxide and
2,5-Bis(3,5-di-tert-butyl-4-hydroxyphenyl)-Mixture and Pure Isomers To a stirred solution of the mixture of isomers prepared in Example 1 (11.0 grams, 0.02 mole) in 50 ml. of methylene chloride at 10° C was added dropwise over a 20-minute period a solution of 85% m-chloroperbenzoic acid (8.53 grams, 0.042 mole) in 100 ml. of methylene chloride. During the addition, the temperature was kept at 10° C by use of an ice bath. After the addition was complete, the mixture was stirred at 10° C for 2 hours. A 5% aqueous sodium carbonate solution was added and the two layers separated. The organic layer was washed with water, dried over anhydrous sodium sulfate, filtered and evaporated in vacuo to give 11.1 grams of a crude sulfone mixture. The mixture was purified by dry column chromatography over silica gel using chloroform as a solvent followed by recrystallization from benzene/hexane to yield 5.8 grams of purified sulfone mixture melting at 288°–291° C (dec.). (Compound 3 = Mixture)

Calc'd for $C_{36}H_{54}O_4S$: C, 74.18; H, 9.34; S, 5.50. Found: C, 74.53; H, 9.27; S, 5.42.

2,6-Bis(3,5-di-tert-butyl-4-hydroxyphenyl)-9-thiabicyclo[3.3.1]nonane-9,9-dioxide A stirred solution of 2,6-bis(3,5-di-tert-butyl-4-hydroxyphenyl)-9-thiabicyclo[3.3.1]nonane-9-oxide, (1.13 gram, 0.0021 mole in 8 ml of methylene chloride was treated at 10° C with the dropwise addition over a 10 minute period of a solution of 85% m-chloroperbenzoic acid (0.426 gram, 0.0021 mole) in 5 ml of methylene chloride. After addition was complete, the mixture was stirred at 10° C for two hours. The mixture was treated with 5% aqueous sodium carbonate solution. The organic layer was then separated, washed with water, dried over anhydrous sodium sulfate, filtered and evaporated to yield 1.1 gram of the above named pure [3.3.1]nonane sulfone product, melting at 295°–300° C (dec.).

2,5-Bis(3,5-di-tert-butyl-4-hydroxyphenyl)-9-thiabicyclo[4.2.1]nonane-9,9-dioxide Using essentially the same procedure described above for making the [3.3.1]nonane sulfone isomer, 0.3 gram of 2,5-bis(3,5-di-tert-butyl-4-hydroxyphenyl)-9-thiabicyclo-[4.2.1]nonane-9-oxide dissolved in 5 ml of methylene chloride was oxidized with 0.113 gram of 85% m-chloroperbenzoic acid in 4 ml of methylene chloride at 10° C. After appropriate work-up, 0.3 gram of the above named pure [4.2.1]-nonane sulfone product, melting at 296°–300° C (dec.), was obtained.

EXAMPLE 4

Unstabilized polypropylene powder (Hercules Profax 6501) was thoroughly blended with 0.2% by weight of the indicated stabilizer compound. Also prepared were samples of polypropylene containing 0.1% by weight of the same stabilizer and 0.3% by weight of distearyl β-thiodipropionate (DSTDP). The blended materials were then milled on a two-roll mill at 182° C for 10 minutes after which time the stabilized polypropylene was sheeted from the mill and allowed to cool.

The milled polypropylene sheets were then cut into pieces and pressed for 7 minutes on a hydraulic press at 218° C and 275 psi (19.25 Kg/cm$^2$) pressure. The resulting plaques of the 25 mil (0.635 mm) thickness were tested for resistance to accelerated aging in a forced draft oven at 150° C. When the plaques showed the first signs of decomposition (e.g., cracking or brown edges), they were considered to have failed. The results are shown in Table I below.

Table I

| Oven Aging of Polypropylene Plaques | |
|---|---|
| Percent Stabilizer | Hours of Failure |
| Unstabilized Polypropylene | 3 |
| 0.3% DSTDP only | 100 |
| 0.2% Compound 1 | 250 |
| 0.1% Compound 1 + 0.3% DSTDP | 825 |
| 0.2% Compound 2 | 220 |
| 0.1% Compound 2 + 0.3% DSTDP | 910 |
| 0.2% Compound 3 | 110 |
| 0.1% Compound 3 + 0.3% DSTDP | 850 |

The compounds 1, 2 and 3 are effective, particularly, when synergized with a thioester co-stabilizer such as DSTDP.

Although the compounds of this invention are effective in the absence of a thio ester co-stabilizer, their effectiveness is appreciably enhanced by the presence of such co-stabilizers.

EXAMPLE 5

Test specimens were prepared exactly as described in Example 4 except that the stabilized polypropylene contained 0.2% by weight of the various esters of this invention and 0.5% by weight of 2-(2-hydroxy-3,5-di-tert-butylphenyl)-5-chloro-2H-benzotriazole as a co-stabilizer. Results of accelerated aging tests in a forced draft oven at 150° C are shown in Table II below:

Table II

| Compound Number (plus co-stabilizer) | Oven Aging at 150° C Hours to Failure |
|---|---|
| Unstabilized Polypropylene | 3 |
| 1 | 230 |
| 2 | 210 |
| 3 | 100 |

This co-stabilizer, useful in affording UV light protection, has no significant effect either positive or negative on oven aging data.

EXAMPLE 6

Test specimens were prepared exactly as those described in Example 5 except that the milled polypropylene sheets were cut into pieces and pressed for 3 minutes on a hydraulic press at 218° C and 275 psi (19.25 kg/cm$^2$) pressure. The resulting sheet of 5 mil (0.127 mm) thickness was tested in a fluorescent sunlight black light environment with the development of carbonyl absorption in the infrared spectrum at the 585 millimicron wavelength being the measure of stabilization protection afforded by the stabilizers present in the polypropylene. Failure was taken as the hours required to cause the carbonyl absorption to reach a value of 0.5. Such a value correlates with the reduction of physical properties of the polypropylene pellicle to unacceptable levels. The results are set out in Table III.

Table III

| Compound Number (plus co-stabilizer described in Example 5) | Fluorescent Sunlight Black Light Test Hours to Failure (0.5 Carbonyl Absorption) |
|---|---|
| Unstabilized polypropylene | 225 |
| 1 | 890 |
| 2 | 1040 |
| 3 | 1390 |

EXAMPLE 7

Sligh Oil Oxidation Test

This test is directed at evaluation of antioxidants in preventing the oxidation of mineral oil at elevated temperature (150° C) under static conditions in the absence of catalytic metals.

To a Sligh oxidation flask fitted with a U-tube, mercury manometer modified by stainless steel and tungsten wires leading to an automatic electric timing device was added 10 grams of mineral oil (Primol 355, USP, Exxon) containing 0.1% by weight of Compound 1 mixture. The Sligh oxidation flask was thoroughly cleaned with chromic acid prior to use, rinsed and dried. The mercury manometer was also thoroughly cleaned, had 2 grams of Linde molecular sieves to absorb water and plugged with glasswool at the joint leading to the flask. The flask containing the mineral oil and stabilizer was flushed with dry oxygen for 1 minute introducing the oxygen near the bottom of the flask before the mercury manometer was firmly attached to the flask. The flask was then immersed in a constant temperature oil bath set at 150° C.

The electric timer was then attached to the manometer. After 30 minutes heating to achieve an initial equilibrium, the upper stainless steel wire is immersed 7.5 cm into the mercury. Heating the flask and contents was continued until the oil absorbed sufficient oxygen to cause a pressure drop of 15 cm of mercury. At this point the stainless steel wire broke contact with the mercury and the time was recorded. This time required for reaching the pressure drop was a relative measure of the effectiveness of the stabilizer in preventing oxidation of the mineral oil the results are seen in Table IV.

Table IV

| Stabilizer (0.1% by weight) | Sligh Oil Oxidation Test Hours to Failure (15 cm drop in oxygen pressure) |
|---|---|
| None | 2.2 |
| Compound 1 | 54.1 |
| Compound 2 | 51.3 |
| Compound 3 | 17.3 |
| BHT* | 31.5 |
| DLTDP** | 25.9 |

*BHT is 2,6-di-tert-butyl-4-methyphenol
**DLTDP is dilauryl β-thiodipropoionate

While all the 9-thiabicyclononanes were effective antioxidants in this test, Compound 1 mixture and Compound 2 mixture were particularly effective, far better than BHT commonly used as an antioxidant for oils.

EXAMPLE 8

Rotary Bomb Oxidation Test

This ASTM test D 2272/IP229/68T comprises a rapid means for estimating the oxidation stability of turbine oils. The test oil, water and copper catalyst coil, contained in a covered glass container, were placed in a copper bomb equipped with a pressure gauge. The bomb was charged with oxygen to a pressure of 90 psi (6.3 Kg/cm$^2$), placed in a constant-temperature oil bath set at 150° C and rotated axially at 100 rpm at an angle of 30° from the horizontal. The time for the test oil to react with a given volume of oxygen was measured, completion of the time indicated by a specific drop in pressure. The time required for the bomb pressure to drop by 25 psi (1.75 Kg/cm$^2$) was taken as indicating completion of the induction period of oxidation of the oil.

Following this induction period when heating is continued, oxidative decomposition begins to occur and can be seen by a rise in system pressure. The time required for the bomb pressure to reach 125 psi (8.75 Kg/cm$^2$) is a further indication of any residual stabilization activity afforded the turbine oil.

The turbine oil containing 0.5% by weight of Compound 1 mixture was evaluated as seen on Table V.

Table V

| Stabilizer (0.5% by weight) | Time (min.) for Bomb Pressure to Decrease to 25 psi (1.75 Kg/cm$^2$) | Time (min.) for Bomb Pressure to Rise to 125 psi (8.75 Kg/cm$^2$) |
|---|---|---|
| None | 20 | 25 |
| Compound 1 | 130 | 153 |
| BHT* | 120 | 126 |
| Commercial Stabilizer** | 106 | 112 |

*BHT is 2,6-di-tert-butyl 4-methylphenol
**4,4'-methylenebis(2,6-di-tert butylphenol)

EXAMPLE 9

Stabilizer for Turbine Oil in Presence of Copper

To 250 grams of a base stock turbine oil (Mobil XRL951) was added 0.5% by weight of compound mixture 1. The matieral was heated on a hot plate with sitrring until the stabilizer dissolved at a temperature of 262° F (128° C). A strip of freshly polished copper foil (1 inch × 3 inches × 0.005 inch; 2.54 cm × 7.62 cm × 0.127 mm) was added to the solution of the stabilizer in the turbine oil in a 400 ml beaker. The system was oven aged at 340° F (171° C) in a forced draft oven (Blue M Model Number POM 2538, air flow 118 fpm (36 mpm)).

After an initial 50 hous of aging, a 15 gram sample of oil was removed and titrated for acid number using alcoholic potassium hydroxide according to ASTM procedure D-664-38 using pH10 as the end point.

Samples were taken at subsequent 24-hour intervals with the formation of sludge (if any) recorded with the acid number. Results are shown below in Table VI.

Table VI

| Stabilizer (% Conc by Weight) | Turbine Oil Stabilization (Mobil XRL 951) | |
|---|---|---|
| | Hours to Acid Number of 0.2 | Hours to First Sign of Sludge |
| None | 50 | >122 |
| Compound 1 (0.5) | 111 | >122 |
| BHT* (1.0) | 77 | >122 |

*BHT is 2,6-di-tert-butyl-4-methylphenol

Compound 1 exhibits better stabilization in protecting turbine oil against the undesirable formation of corrosive acidity as seen by the longer time needed for the acid number of 0.2 to develop while at the same time preventing the equally undesirable formation of sludge from occurring. Compound 1 mixture is a particularly good stabilizer for turbine oils as seen from this rigorous test procedure.

EXAMPLE 10

Processing Stabilizer for Linear Polyethylene

Unstabilized linear polyethylene (Marlex 5202, Phillips Petroleum Company) was solvent blended in methylene chloride with 0.02% by weight of the resin of 2,6-bis(3,5-ditert-butyl-4-hydroxyphenyl)-9-thiabicyclo[3.3.1]nonane and 2,5-bis(3,5-di-tert-butyl-4-hydroxyphenyl)-9-thiabicyclo[4.2.1]nonane mixture and then vacuum dried. The resin was then extruded at 550° F (287.8° C) using a ¾ inch (1.905 cm) extruder having a 24:1 L/D ratio. The melt flow rate of a sample of the resin was determined after each extrusion according to ASTM test D-1238. Polyethylene stabilized with the above mixture of compounds was found to undergo less change in melt flow rate than unstabilized polyethylene and to exhibit essentially the same change in melt flow rate as polyethylene stabilized by a like amount (0.02% by weight) of 2,6-di-tert-butyl-4-methylphenol, BHT.

EXAMPLE 11

Pellets (500 g) of unstabilized nylon-6,6 (Zytel 101, DuPont) are placed in a Kitchen Aid Mixer. With mixing a solution of 0.5% (based on the weight of nylon) of 2,6-bis(3,5-di-tert-amyl-4-hydroxyphenyl)-9-thiabicyclo[3.3.1]nonane and 2,5-bis(3,5-di-tert-amyl-4-hydroxyphenyl)-9-thiabicyclo[4.2.1]nonane in 20 ml of methylene chloride is added slowly. Sodium hypophosphite (0.5 gm) is dissolved in 20 ml of water and added slowly with mixing to the nylon pellets after the antioxidant solution has been added and most of the methylene chloride has evaporated. The stabilized pellets are dried at 80° C at <<1 mm Hg. for 4 hours.

The polyamide formulation is extruded at 600° F (315.6° C) through at ¼ inch (0.635 cm) die into a rod which is water cooled and chopped into pellets. A ¾ inch (1.905 cm) Brabender extruder, equipped with a nylon screw, is used. The pellets are dried at 80° C at <1 mm for 4 hours.

The dried pellets are compression molded into 5 mil (0.127 mm) thick film by pressing at 290° C for 4 minutes at 6000 psi (57.75 Kg/cm$^2$). The films are oven aged at 150° C in a forced draft oven and samples are removed periodically. The specific viscosity of the samples are determined using a 1% formic acid solution at 25° C. The sample stabilized with the above noted stabilizers required longer aging time to reduce its viscosity by one-half than the unstabilized sample.

EXAMPLE 12

Unstabilized high impact polystyrene resin is dry blended with 0.1% by weight of the resin 2,6-bis(3,5-di-tert-octyl-4-hydroxyphenyl)-9-thiabicyclo[3.3.1]nonane and 2,5-bis(3,5-di-tert-octyl-4-hydroxyphenyl)-9-thiabicyclo[4.2.1]nonane. The resin is then extrusion compounded on a 1 inch (2.54 cm) 24/1=L/D extruder, melt temperature 500° F (260° C) and pressed for 7 minutes at a temperaure of 163° C and a pressure of 2000 psi (140 Kg/cm$^2$) into a sheet of uniform thickness of 100 mil (2.54 mm). The sheets are then cut into plaques of 2 inch × 2 inch (5.08 cm × 5.08 cm). The plaques are then oven agen at 80° C and color measurements made periodically using a Hunter Color Difference Meter Model D25. The polystyrene samples stabilized with the above mixture develops the undesirable yellow discoloration substantially later than the time that such discoloration occurred in the unstabilized samples.

EXAMPLE 13

A quantity of SBR emulsion containing 100 g of rubber (500 ml of 20% SBR emulsion obtained commercially from Texas U.S. as Synpol 1500) previously stored under nitrogen, is placed in a beaker and stirred vigorously. The pH of the emulsion is adjusted to 10.5 with 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumbrubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg finally to constant weight under high vacuum (<1 mm ) at 40° to 45° C.

The dried rubber (25 g) is heated under nitrogen at 125° C in a Brabender mixer and to this is added with mixing 0.1% by weight of 2,6-bis(3,5-di-tert-amyl-4- hydroxyphenyl)-9-thiabicyclo[3.3.1]nonane-9-oxide and 2,5-bis(3,5-di-tert-amyl-4-hydroxyphenyl)-9-thiabicyclo[4.2.1]-nonane-9-oxide.

Portions of the rubber are oven aged at 100° C. At various intervals gel content is determined on the rubber. The rubber stabilized with the above mixture shows much less gel formation than the unstabilized sample.

EXAMPLE 14

To 50 g of polyacetal resin containing 0.1% of an acid scavenger, dicyandiamide, is added 0.2% by weight of 2,6-bis(3,5-di-tert-octyl-4-hydroxyphenyl)-9-thiabicyclo[3.3.1]nonane-9-oxide and 2,5-bis(3,5-di-tert-octyl-4-hydroxyphenyl)-9-thiabicyclo[4.2.1]nonane-9-oxide and milled for 7 minutes at 200° C in a Brabender Plastirecorder. The milled formulation is subsequently pressed into a 40 mil (1.016 mm) sheet at 215° C at 350 psi (24.5 Kg/cm²) for 90 seconds then cooled quickly in a cold press at 350 psi (24.5 Kg/cm²). The stabilized sheets are then remolded for 2 minutes at contact pressure and for 3 minutes at 300 psi (21 Kg/cm²) at 215° C to give plaques 1.5 inches × 1.5 inches × 125 mil (3.81 cm × 5.715 cm × 3.175 mm). The plaques are aged in the oven at 60° C and the weight loss of the specimen is determined periodically until a 4% weight loss is reached. The stabilized sample takes a much longer time to reach this 4% weight loss than does the unstabilized sample.

EXAMPLE 15

Unstabilized, thoroughly dried polyethylene terephthalate chips are dry blended with 1.0% by weight of 2,6-bis[3,5-bis(α,α-dimethylbenzyl)-4-hydroxyphenyl]-9-thiabicyclo[3.3.1]nonane-9,9-dioxide and 2,5-bis[3,5-bis(α,α-dimethylbenzyl)-4-hydroxyphenyl]-9-thiabicyclo[4.2.1]nonane-9,9-dioxide, 60/10 denier multifilament is melt spun at a melt temperature of 290° C and cold oriented 3 to 1. The oriented fibers are wound into skeins and oven aged at 140° C. The stabilized material exhibits greater retention of tensile strength after 24 hours then the unstabilized material.

EXAMPLE 16

A stabilized high temperature lubricating oil is prepared by incorporating 0.05% by weight of 2,6-bis(3,5-di-tert-butyl-4-hydroxyphenyl)-9-thiabicyclo[3.3.1-]nonane and 2,5-bsi(3,5-di-tert-butyl-4-hydroxyphenyl)-9-thiabicyclo-[4.2.1]nonane to the lubricant which comprises diisoamyl adipate. The stabilized composition is compared with the unstabilized lubricant by heating at 175° C in the presence of air and metallic catalysts according to the test method described in Military Specification Mil-I-7808c. After 72 hours, the blank containing no stabilizer contains more sludge and has greater viscosity than the stabilized lubricant.

What is claimed is:

1. A compound having the formula

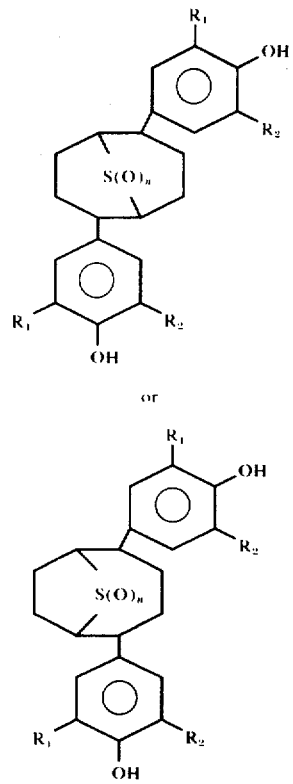

wherein
$R_1$ and $R_2$ are each independently tertiary alkyl of 4 to 8 carbon atoms, or α,α-dimethylbenzyl, and
n is 0 to 2, or a mixture of said isomeric compounds wherein the same hindered phenolic moiety is attached to either the 5 or 6 carbon of the 9-thiabicyclononane ring.

2. A compound according to claim 1 wherein $R_1$ and $R_2$ are each independently tertiary alkyl of 4 to 8 carbon atoms, and
n is 0 to 2.

3. A compound according to claim 2 wherein n is 0 to 1.

4. A compound according to claim 1 wherein $R_1$ and $R_2$ are each tert-butyl.

5. A compound according to claim 4 wherein n is 0 to 1.

6. The compound according to claim 1 which is 2,6-bis(3,5-di-tert-butyl-4-hydroxyphenyl)-9-thiabicyclo[3.3.1]nonane; 2,5-bis(3,5-di-tert-butyl-4-hydroxyphenyl)-9-thiabicyclo[4.2.1]nonane or a mixture thereof.

7. The compound according to claim 1 which is 2,6-bis(3,5-di-tert-butyl-4-hydroxyphenyl)-9-thiabicyclo-[3.3.1]nonane-9-oxide; 2,5-bis(3,5-di-tert-butyl-4-hydroxyphenyl)-9-thiabicyclo[4.2.1]nonane-9-oxide or a mixture thereof.

8. The compound according to claim 1 which is 2,6-bis(3,5-di-tert-butyl-4-hydroxyphenyl)-9-thiabicyclo[3.3.1]nonane-9,9-dioxide; 2,5-bis(3,5-di-tert-butyl-4-hydroxyphenyl)-9-thiabicyclo[4.2.1]nonane-9,9-dioxide or a mixture thereof.

9. A composition of matter comprising an organic material subject to degradation and from 0.01 to 5% by weight of a stabilizing compound of claim 1.

10. A composition of claim 9 containing additionally from 0 to 2% by weight of a thio co-stabilizer having the formula

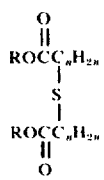

wherein R is alkyl of 6 to 24 carbon atoms and $n$ is 1 to 6.

11. A composition of claim 9 containing additionally from 0 to 5% by weight of a light stabilizer.

12. A composition of claim 9 wherein the stabilizing compound is 2,6-bis(3,5-di-tert-butyl-4-hydroxyphenyl)-9-thiabicyclo[3.3.1]nonane, 2,5-bis(3,5-di-tert-butyl-4-hydroxyphenyl)-9-thiabicyclo[4.2.1]nonane or a mixture thereof.

13. A composition of claim 9 wherein the organic material is polyolefin or hydrocarbon.

14. A composition of claim 13 wherein the hydrocarbon is a mineral turbine oil.

* * * * *